United States Patent [19]

Langberg

[11] 3,967,994
[45] July 6, 1976

[54] METHOD OF INSPECTION FOR SPLICES USED FOR JOINING WEBS IN A MANUFACTURING PROCESS

[75] Inventor: Edwin Langberg, Mount Laurel, N.J.

[73] Assignee: Langberg Associates, Inc., Mount Laurel, N.J.

[22] Filed: Oct. 9, 1974

[21] Appl. No.: 513,302

[52] U.S. Cl. .................................. 156/64; 156/157; 156/378; 156/380; 242/58.4; 242/58.5; 324/58.5 R; 324/58.5 C; 333/83 R
[51] Int. Cl.² ........................................ G01N 23/00
[58] Field of Search .................. 324/58.5 R, 58.5 C; 242/58.4, 58.5; 156/64, 351, 378; 333/83 R

[56] References Cited
UNITED STATES PATENTS

| | | | |
|---|---|---|---|
| 3,132,204 | 5/1964 | Giellerup | 156/275 |
| 3,146,431 | 8/1964 | Betts | 156/64 |
| 3,567,534 | 3/1971 | Kushiro | 156/378 |
| 3,637,153 | 1/1972 | King | 242/58.4 |

Primary Examiner—Edward G. Whitby
Attorney, Agent, or Firm—Pennie & Edmonds

[57] ABSTRACT

A method is disclosed for maintaining continuity in a manufacturing process employing one or more webs provided in the form of shorter raw material webs in which the raw material webs are spliced together end-to-end as the preceeding web of the same material is depleted, and those web portions containing splice material are detected at a later stage of the process by a microwave detector. A microwave detector is provided in the form of a slotted microwave cavity through which the web may be continuously passed to detect the splicing tape in the web.

5 Claims, 7 Drawing Figures

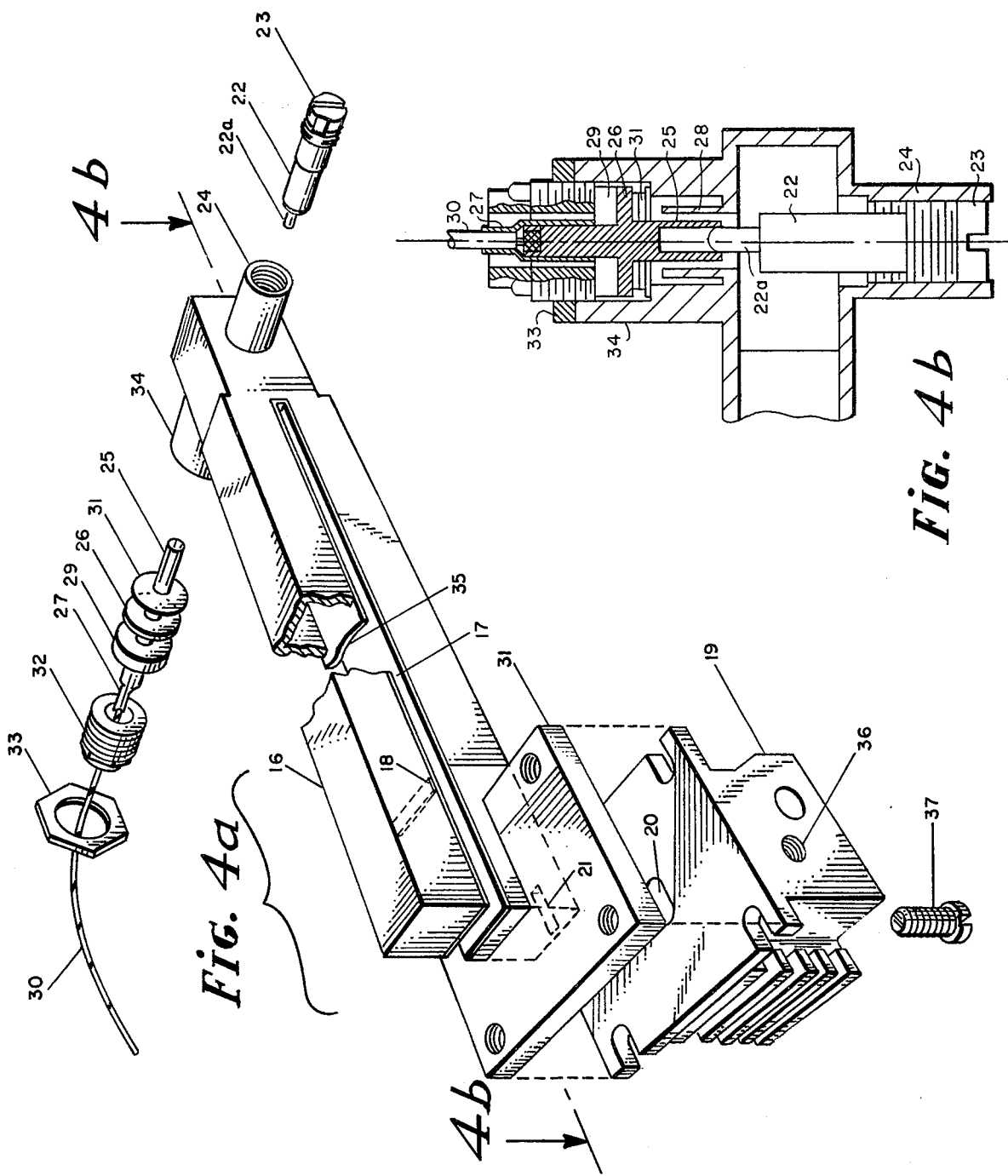

METHOD OF INSPECTION FOR SPLICES USED FOR JOINING WEBS IN A MANUFACTURING PROCESS

BACKGROUND OF THE INVENTION

Many manufacturing processes employed in producing plastics, textiles, paper and composites of them, as well as other generally non-metallic goods, involve forming or processing the product from continuous web or webs. The individual webs are wound on reels, and as each reel is processed in the manufacturing machinery, the web on the next reel must be spliced to it, in order to maintain web continuity, and avoid shutting down and restarting the machinery.

The end product must often be screened to reject any of it containing splicing material. In some cases this screening or inspection can be performed optically, e.g. by photosensors which detect specific properties such as color, reflectivity, or the like, designed into the splicing tape for that purpose.

A splicing tape for industrial application must have an adhesive with good bonding properties. The tape itself must be thin, strong and preferably elastic. The requirement of thinness is dictated by the clearance between rollers in the manufacturing machinery. In order not to damage the machine, the tape thickness must be much smaller than the web thickness, so that the splice can go through the machinery essentially the same way as the unspliced web.

A popular splicing tape consists of a 1 mil polyester film coated with approximately 1 mil of adhesive. A vacuum evaporated layer of aluminum approximately 100 microinches thick is often added for splice detection by optical reflectivity. Such a tape will be referred to as aluminized splicing tape.

An example of a composite process using aluminized splicing tape for a continuous feed of web material is the manufacture of pre-packaged adhesive bandages. Primary raw materials come in a web which may be as wide as six feet. In primary processing the wide web is slit into narrow. e.g., 1 inch, strips which are wound on individual reels. In the slitting operation several wide reels are spliced together to get the required length of the narrow strip.

The various materials in form of web strips are then fed continuously into bandage manufacturing machinery by splicing the end of one roll to the beginning of the next. The machinery can perform bonding, perforation, folding, and interleaving of the individual web strips until, in the last stage, the composite is cut into individual bandages. It is clear that the end product can contain splices originating from the primary slitting operation or from subsequent joining of the narrow web strips.

In the bandage manufacture, and in many other instances, the product is such that the splices on it may be covered up and hence are optically inaccessible for detection (referred to herein as an interior splice). Prior to the present invention, no known inspection technique was capable of satisfactorily detecting aluminized splicing tape in the interior of a product, i.e. when it was not optically accessible. In limited instances, metal detectors have been employed to detect interior aluminized splices in the end product. However, ordinary metal detectors, which operate in the megahertz region, have not generally met with industrial acceptance because of sensitivity to extraneous conditions such as moisture. The reliability of internal splice detection by ordinary metal detectors could be improved if much thicker metal coating, or a metal tape, could be used for splicing so that the metal thickness would be comparable with the skin depth of the current generated by such detectors. However, as pointed out earlier, increased thickness of splicing tape is undesirable and often unacceptable.

SUMMARY OF THE INVENTION

In accordance with the invention, web stock is spliced into a longer or a continuous web for processing with a splicing tape having a thin layer (e.g. 100 microinches) of metal such as aluminum deposited on it. Splices are detected at an appropriate stage of manufacture by microwave detector operating in the x-band (5–11 GHz) region. At X-band the skin depth is less than 100 microinches, permitting excellent detection sensitivity even for a very thin layer of metal.

In accordance with the preferred embodiment of the invention, the detector is a microwave cavity slotted on three contiguous sides long lines parallel to current flow in the cavity walls, facilitating easy insertion of the web into the cavity and permitting the web, over a part or the whole web width, to run through the cavity. The cavity, in the absence of a splice, is operated at resonance. The splice, when present, lies in the plane of the electric field vector. The output signal, derived from a diode detector within the cavity, exhibits a marked drop in the presence of the aluminized splicing tape due to detuning of the cavity.

DESCRIPTION OF THE DRAWINGS

The invention will be more fully described in connection with the annexed drawings, in which:

FIG. 3b is a cross-sectional view of the cavity illustrated in FIG. 3a;

FIG. 4a is a schematic perspective view of a slotted microwave cavity in accordance with the invention;

FIG. 4b is a cross-sectional view of the diode tuning mechanism in the cavity of FIG. 4a;

DETAILED DESCRIPTION OF THE PREFERRED EMBODIMENT OF THE INVENTION

Figure 1:
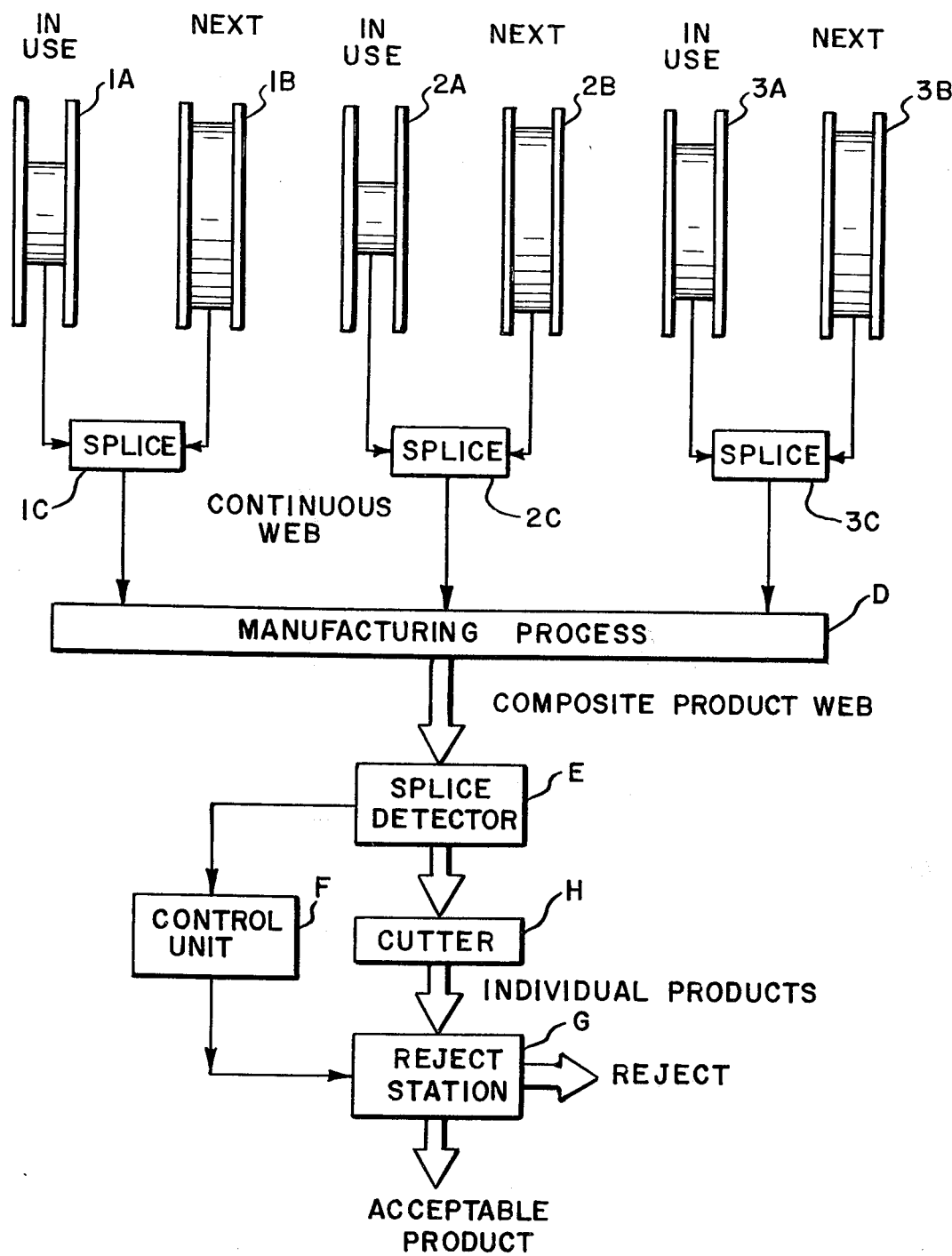
FIG. 1 is a schematic block diagram of the method of the invention.

FIG. 1 illustrates by way of a manufacturing flow diagram an industrial process employing the method of the present invention. The manufacture may be based on a continuous web operation, or for that matter any operation involving the processing of webs, in which the raw material webs are supplied in discrete lengths which are joined or spliced together to form a longer of a continuous web or webs and in which the splices employed to join the discrete webs are to be detected at a later stage of the manufacturing process. A typical example, shown in FIG. 1, involves the necessity for rejecting all product containing splice material at some final or near final stage of manufacture.

In FIG. 1, discrete webs of three different raw materials, 1, 2 and 3 are spliced end to end to form a continuous web. i.e. the beginning of web 1B is spliced to the end of web 1A, as each raw material web is consumed in the process, with splicing steps illustrated in boxes 1C, 2C and 3C. This splicing is conventionally done manually. The spliced raw material webs then proceed through the process, indicated as box D, and the process output in the form of a composite web undergoes the step of microwave detection, illustrated in box E. The microwave detector output is coupled to operate automatic apparatus (F and G), compatible with the particular product, responsive to detection of splicing material for rejecting product containing portions of the composite web with splicing material, and passing the remaining product which is free of splicing material.

The web in process D may be any one employing materials which are non-metallic or which at least have conductivities sufficiently different from that of the metal deposited on the splicing tape to permit adequate discrimination by the microwave detector. In the manufacture of sterile adhesive bandages as mentioned above, for example, the raw material webs are generally adhesive-coated plastic sheeting, gauze and paper materials.

The splicing tape employed in accordance with the invention may be any adhesive tape not otherwise incompatible with the particular process in which it is to be employed and upon which a thin layer of conductive material, preferably metal, is deposited. An aluminized splicing tape useful in many processes in accordance with the invention is adhesive coated polyester tape, approximately 1 mil thick having deposited on it by conventional techniques such as vacuum evaporation a uniform film of aluminum about 100 microinches thick. The aluminum coating adds virtually nothing to the thickness of the tape and in no way impairs its flexibility. The tape may alternatively be used to mark the web or webs used in the process at points which it is desirable to locate at a later process stage when the markers may not be readily visible but are easily located by microwave detection.

In some instances, it may be desirable to detect splices after the component web or webs have already been cut into discrete products. The discrete products may then be conveyed through the microwave detector on a moving belt or similar conveyor, and sorted or handled according to whether the discrete units contain or do not contain the metallized tape.

In the operation of an aluminized tape splice detector, the time-varying electromagnetic field penetrates the aluminum film. It can be shown that the magnitude of the surface field $E_o$ which penetrates through a metal film is:

$$E = E_o \exp(-d/\delta),$$

where $d$ is the thickness of the film and $\delta$ is the skin depth.

The skin depth is defined as the distance from the surface, for a conductor carrying currents at a given frequency, at which the current density descreased to 28% of the current density at the surface.

The skin depth $\delta$ is given by:
$\delta = (\pi f \mu \sigma)^{-1/2}$
where $f$ is the frequency in Hz,
$\sigma$ is the conductivity in mho, and
$\mu$ is the permeability in Henry/m.

Figure 2:
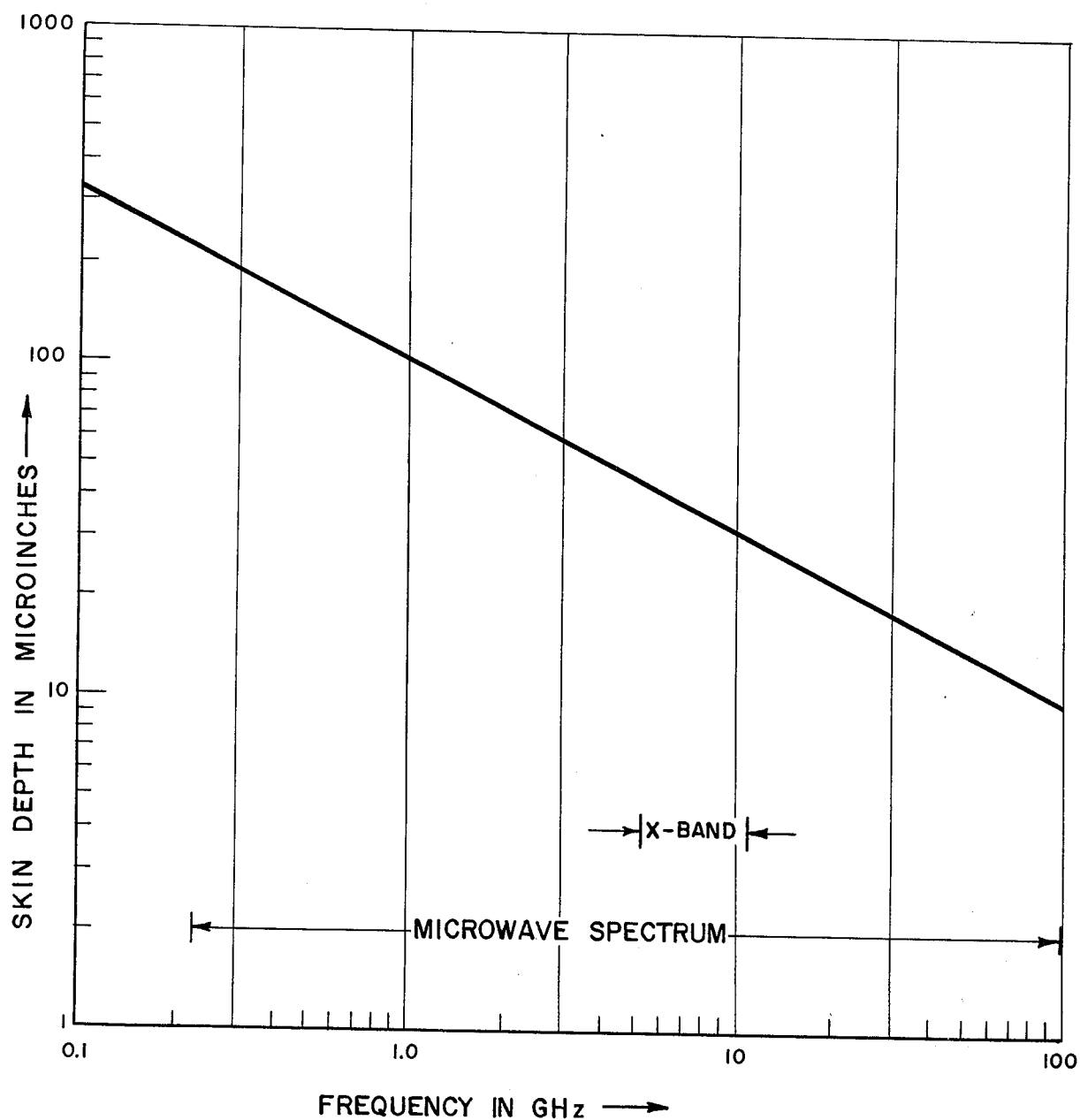
FIG. 2 shows the microwave field skin depth in an aluminum layer as a function of the microwave frequency.

Based on this formula, the skin depth for aluminum is plotted in FIG. 2 in the frequency interval between 0.1 and 100 GHz, which coincides with the microwave spectrum. It can be seen that the skin depth of 100 microinches is reached at 1 GHz. Therefore, any frequency above 1 GHz is satisfactory for detection of aluminized tape splices where the aluminum layer is thicker than about 100 microinches. At substantially lower frequencies the aluminum film is essentially transparent to the field. Aluminized tape splices can be optimally detected in the frequency range about 1 GHz.

The choice of a specific band within this microwave region is dictated by considerations of economy and convenience. X-band (5.2–10.9 GHz) components are readily available in view of their extensive application in radar and communication. Further, the size of X-band components is convenient for splice detection. These considerations lead to the selection of X-band for splice detection.

Microwave detection in accordance with the present invention may be carried out by many such microwave web detectors previously employed. Such detectors are conventionally used in industrial processes to measure variations in the moisture content or other properties of a continuous product stream, to measure variations in the cross sectional area of a conductor and for other purposes. Such detectors conventionally involve passing the product to be detected through a wave guide, or irradiating it from one side with microwave energy which is detected at the other side of it by a microwave receiver. In certain applications, for example, those related to electron paramagnetic resonance spectroscopic examination, microwave cavities are employed as detectors. Microwave cavities are for most detection applications superior to wave guides or other similar apparatus, but have generally not been suitable for web control because of the difficulty of moving webs through them. As a result, microwave cavity detectors have tended to be somewhat complex, requiring frequency sweep drives and other comparitively complex support systems (see e.g. U.S. Pat. No. 3,458,808). As detectors in connection with continuous webs, for example, a significant problem has been the difficulty of initially threading the web through the detector, since access to the web path through the detector is generally limited by the necessity of minimizing openings in the cavity walls. Measurement or detection by microwave cavity, rather than by a wave guide or with discrete transmitting and receiving apparatus on opposite sides of the web to be detected (open beam measurement), has several advantages. In a cavity, the microwave energy is reflected many times through the material being detected, permitting a much higher detection sensitivity (high Q) than with techniques in which it passes only once through the material. Moreover, open beam measurements generate a much higher stray field than a cavity measurement, and may exceed the stringent limitations set by the F.C.C. on radio frequency interference measurements as well as the maximum electromagnetic dosages limited by health regulations. Particularly, cavity detection permits much more accurate and localized control of the microwave field than is possible with other microwave techniques. Wave guide detection or measurement, while facilitating containment of the microwave energy, is relatively insensitive compared with cavity measurement, and the necessity of threading a moving web through opposite sides of the wave guide in order to load the detector initially (see e.g. U.S. Pat. No. 3,034,046) renders such techniques generally unsuitable for industrial application.

In accordance with a preferred embodiment of the invention, a microwave cavity detector is provided for use in the method described above which is highly sensitive, needs only relatively simple drive and detection circuits, and permits easily threading a web through it both at the start-up of the process and in the event of web breakage or damage. Previous cavity detectors have imposed severe limitations and have required tedious operations for rethreading the web through the cavity, precluding their use for many web measurement and detection applications. These limitations are completely avoided in accordance with the present invention.

Figure 3A:
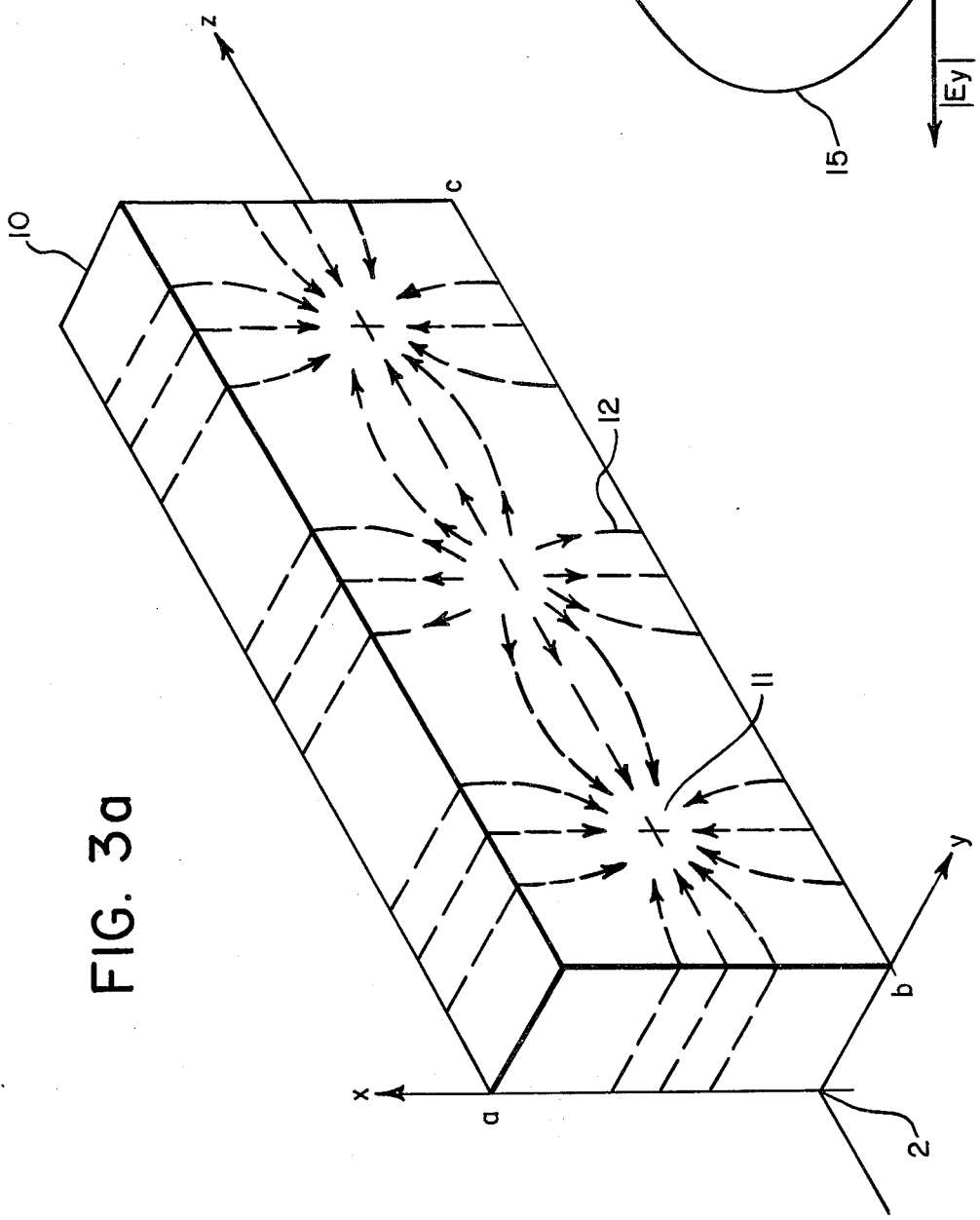
FIG. 3a is a schematic illustration of a conventional closed rectangular cavity in the $TE_{103}$ mode.
Figure 3B:
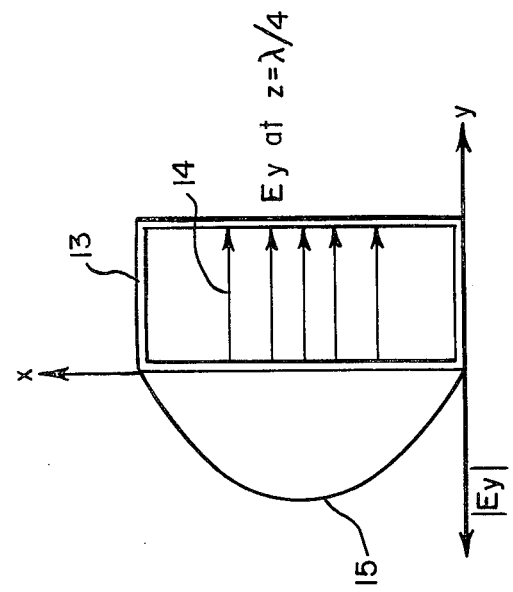

FIGS. 3a and 3b describe a conventional closed rectangular cavity in $TE_{103}$ mode. This figure is used to define the terminology and serves as point of departure for describing an open slot cavity in accordance with the invention shown in FIGS. 4a and 4b. FIG. 3a shows such a conventional cavity 10 formed by a closed off section of rectangular waveguide and operating in the transverse electric (TE) mode. A set of orthogonal coordinal axes defines $x$, $y$ and $z$ directions in the cavity. The resonant mode is defined by the number of half wavelengths $\lambda/2$ along these three coordinate axes. The cavity shown is one-half wavelength in the $x$ direction, has constant field (zero wavelengths) in the $y$ direction, and three half wavelengths in the $z$ direction. Consequently the cavity mode is defined as $TE_{103}$.

For construction of an open cavity it is important to understand the distribution of charges and currents on the inside surface of the closed cavity of FIG. 1. The concentration of charge shown by 11 occurs at a distance $\lambda/4$ from the cavity walls along the $z$ direction. This concentration of charge on the surface corresponds to a maximum electric field on the inside of the cavity, shown in different view in FIG. 3b. The direction of current flow on the surface is shown by lines, such as 12 in FIG. 3a.

FIG. 3b shows the cross-section through the cavity perpendicular to the $z$ axis at a point of maximum electric field i.e. $Z=\lambda/4$. Cavity wall 13 encloses a microwave field. The direction of the electric field is represented by vectors 14. The sinusoid 15 at the left of FIG. 3b represents the amplitude of the electric field as it varies along the $x$ axis.

In accordance with the invention, as shown in FIG. 4a, a slot is cut along lines approximately parallel with the current flow in the related unslotted cavity (FIG. 3), thereby producing a high Q, stable microwave resonance cavity. Cavity 16 thus has a slot 17 cut in the $y$—$z$ plane which is made sufficiently wide (in the $x$ direction) to accommodate the thickness of the moving web to be detected. To form the slot 17, cuts are made in the $y$—$z$ plane at $x=X_1 = ½ (a-d)$ and $x=X_2 = ½ (a+d)$, where $d$ is the width of the slot and $a$ is the cavity width in the $x$ direction. The slot is preferably covered by a 0.010 thick polyolefin tape 35 which has a very low coefficient of friction and good wear resistance, thereby allowing easy passage of web through the cavity.

The slot 17 is cut substantially parallel to the current flow lines in the wall of the FIG. 3 cavity, assuring minimum disturbance of the original (unslotted) resonance mode. Nevertheless, the slot does to a minor extent allow parasitic modes of propagation to arise which do not exist in the unslotted cavity. In order to suppress these modes and to enhance and control the impedance matching of the oscillator and of the detector diode, a narrow conductive strip or strips 18 can be placed at any or all of the nodal points $Z=\lambda/2$, $\lambda, 3\lambda/2$ . . . and extending in the $y$ direction across the waveguide. Preferably two conductive strips are provided at each nodal point, one above the slot as shown and one below it.

The waveguide wavelength of the cavity is also increased by slotting the walls. To offset this effect, the height $a$ of the slotted portion of the cavity may be increased so that it is larger than that $a$ of the unslotted diode holder 17a. The amount by which the cavity height should be increased depends upon the width ($x$-direction) of the slot and may be determined in the same manner as for the matching of an unslotted with a slotted section of waveguide, as set forth for example beginning at page 398 of the *Waveguide Handbook* by K. Marcuvitz, McGraw Hill, 1951. It has been found nevertheless that if the heights $a$ and $a$ are made equal, any slight deviation from resonance resulting therefrom will not detract from the detection capabilities of the cavity.

Unlike the ordinary waveguide, where coupling of the oscillator and detector can be accomplished through the opposing waveguide ends, coupling to the open cavity must be done in a novel manner. A microwave power source, such as a Gunn oscillator, is located in oscillator cavity 19. Its frequency can be adjusted by screw 36. Cavity 19 is coupled through opening 20 to the outside. The coupling of microwave energy into the cavity 16 is accomplished through a slot 21 in the $x=0$ (or $x=a$) wall of the cavity. The length of the coupling slot 21 should be somewhat less than $\lambda/4$, but is not otherwise critical. It is important, however, that the slot 21 begin at $z=0$ in order to effect proper flow of coupling current in the slotted $z=0$ face of the cavity. The oscillator cavity 19 is fastened to a flange 31 by four screws, such as shown by 37.

A microwave detector diode 22 is mounted in the center of the diode holder 17a, of smaller height, $a'$ in the $x$-direction than the height $a$ of cavity 17, which forms by itself a $TE_{101}$ cavity compartment. Diode 22 is joined to a threaded rod 23 which screws into a threaded bushing 24 mounted in the wall of the cavity (as shown in more detail in FIG. 4b), permitting adjustment of the $y$-axis position of the diode by rotation of rod 23 to achieve optimum coupling. The optimum coupling is achieved when the diode output signal is high in the presence of a normal web in the slot (i.e. one free of splice material) and drops significantly when even a small sliver of splicing tape is on the portion of the web within the cavity. The tip 22a of the diode makes contact with a sleeve 25 which is a part of a single metal piece comprising also disc 26 and sleeve 27, which serves as a fastener for output wire 30. Consequently, wire 30 is electrically connected to tip 22a of the microwave detector diode 22 and the signal on it is the rectified microwave signal.

As more clearly shown in FIG. 4b, tube 28 forms a folded half-wavelength coaxial line terminated in a short circuit. This line transforms the opening in the cavity wall, through which lead 22a is connected to the outside, into a very low microwave impedance, allowing proper resonance of the diode holder. Insulated washers 29 and 31 provide the required insulation of the output voltage from the body of the cavity.

Threaded tube 32 and nut 33 serve to fasten the assembly together by threading into housing element 34. The rectified microwave power appears as a voltage on sleeve 27 and the output conductor 30 connected to it.

The output from the diode detector (on wire 30) is preferably connected to a comparator (not shown) which produces a high or low output voltage depending on whether the voltage on output 30 is lower or higher than a pre-set threshold voltage. Such comparators are known and do not in themselves form part of the invention.

The slotted cavity of FIG. 4a may be made to accept virtually any width web by constructing it of sufficient length in the z direction to accommodate the web. For thicker webs, the use of a lower microwave frequency permits the cavity to have a longer x dimension so as to minimize any parisitic modes introduced by the wider slot necessary to accommodate the web thickness. The cavity of FIG. 4a may also be used to measure or detect variations of other parameters of moving webs conventionally detected by microwave open beam, waveguide or cavity techniques, such as moisture content, at a frequency to which the detected parameter is known to be sensitive. This in turn dictates the operating frequency and hence the half-wavelength dimension of the cavity.

Metallized splices and many other web materials are rather thin, and if the microwave electric field is perpendicular to the web, the efficiency of measurement of web properties is poor. Therefore, the cavity shown in FIG. 4a and 4b is constructed to produce an electric field which is substantially parallel to the splice. The electric field in slot 17 is substantially the same as vector 14 in FIG. 3b, which is in the plane of the web.

Figure 5:
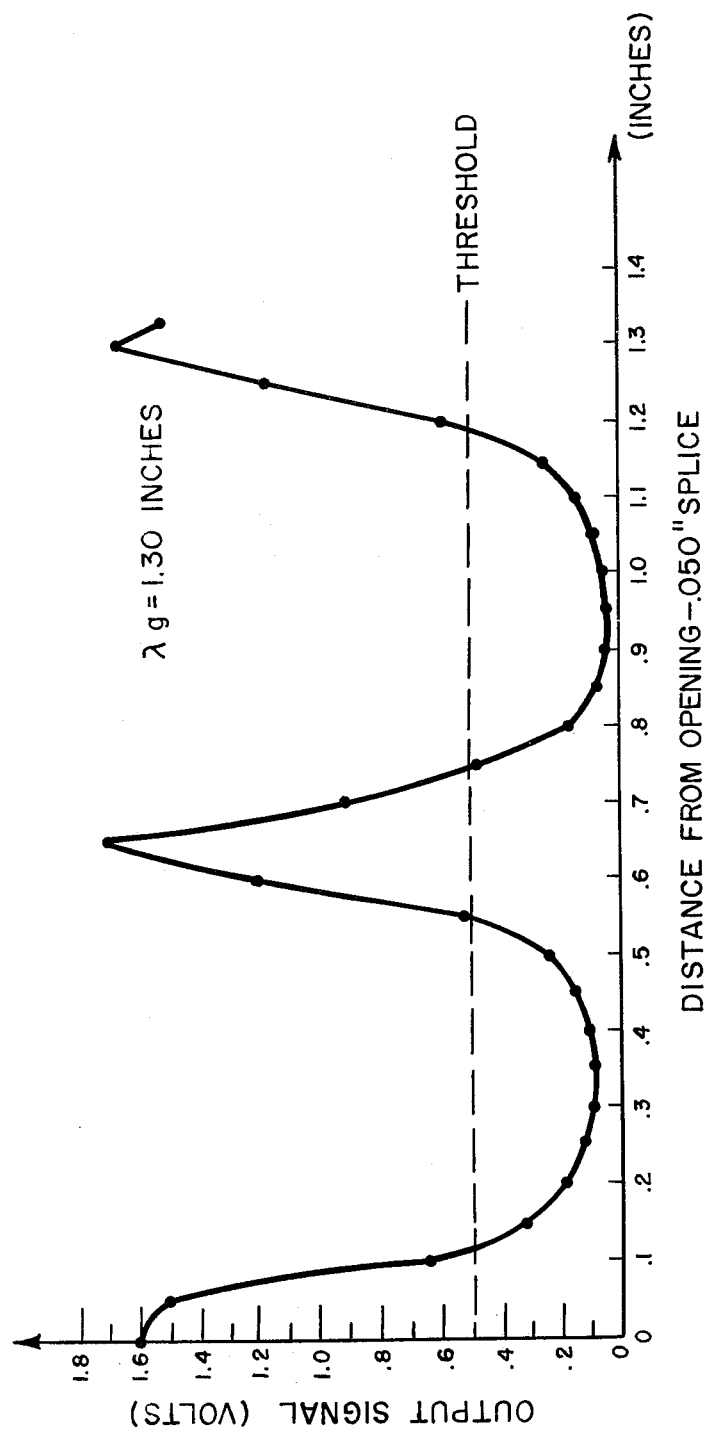
FIG. 5 is a graph showing the detection sensitivity of the cavity of FIG. 4.

A typical measurement characteristic of the cavity of FIG. 4 for the detection of splices on a composite web in a bandage manufacturing process is illustrated in FIG. 5. This is a plot of detector output voltage versus distance of a splice from the cavity opening along the z dimension. Here the web consists of plastic and adhesive backing which has in its center an absorbant gauze pad and is covered by a paper wrapper. The splice is made from an aluminized splicing tape as described above.

The test splice, consisting of a 0.050 inch wide splice strip on the composite web stretching across the cavity, for the purpose of FIG. 5, is moved in the z direction along the cavity. Since detuning of the cavity is accomplished by shorting the electric field $E_y$ by the metal layer of the splice, the maximum sensitivity is at points where $E_y$ is largest. It can indeed be seen from FIG. 5 that the largest output voltage drop occurs when the splice is at the points of maximum electric field, approximately $n\lambda/4$ ($n=1,2\ldots$) from the opening of the cavity. A sliver 0.050 inch of a splice can be formed in cutting or slitting of a larger splice, but generally the remanant of a splice on a product is larger. Therefore in this application of splice detection the variation of sensitivity is of no consequence because the splices cover an area sufficiently large to fall at least partially into the sensitive region of measurement. But if gaps in sensitivity are a problem, one can use two separate (or coupled) cavities side by side along the web, but shifted $\lambda/4$ with respect to each other in the z direction. In this configuration the insensitive region of one cavity coincides with the region of maximum sensitivity of the other and the system eliminates sensitivity gaps.

The threshold level in FIG. 5 is set to 0.5 volts. The composite web without splices causes an output voltage of 1.6 volts which is safely above the threshold level. On the other hand, even small splices reduce the diode output voltage below the threshold level of 0.5 volts, thereby initiating the rejection process.

Other open cavity configurations can be employed for web inspection, following the teaching of this invention that the slot for web passage must be formed parallel to the cavity wall current flow, so that current flow is parallel to the edges of the slot, and that the electric field should be in the plane of the web. The cavities described in this application are of rectangular design. However, slotted cavities according to the invention can alternatively have other geometries such as cylindrical or spherical.

It will be apparent to those familiar with this art that varous modifications may be made in the specific embodiments described herein without departing from the spirit and scope of the invention, which is limited solely in accordance with the following claims.

I claim:

1. A method for maintaining the continuity of a manufacturing process employing one or more webs, each of which is provided in the form of shorter webs of raw material to be fed sequentially into the process as the preceeding web of the same material is depleted, comprising:
   a. splicing successive shorter webs of the same raw material together as each is depleted through use in the process with an adhesive tape having thereon an electrically conductive coating; and
   b. monitoring the web at the output of such process by irradiating it with a microwave frequency electromagnetic field, and detecting variations in said field due to the presence therein of the conductive coating on said tape, thereby permitting identification of portions of such webs containing splices.

2. A method as defined in claim 1 wherein said splicing tape is coated with a layer of metal having a thickness at least substantially equal to the skin depth of the electromagnetically induced current at the microwave frequency used.

3. A method as defined in claim 2 wherein said microwave electromagnetic field has a frequency in the x-band and the metal layer is approximately 100 microinches thick.

4. A method as defined in claim 2 wherein said continuous monitoring is performed by passing such web through a microwave cavity driven at resonance, said cavity having slots in three contiguous walls thereof lying essentially along the lines of current flow in said walls and forming an electric field vector in the plane of the slot, said slot forming a passageway through the cavity into which such web can be readily inserted for continuous movement therethrough, said cavity including a source of electromagnetic radiation and means for detecting the electromagnetic field therein, whereby entry into the cavity of web portions containing such tape causes the detection means to indicate a change in such field.

5. A method as defined in claim 4 wherein said continuous monitoring is performed by a pair of microwave cavities as set forth in claim 4 displaced $\lambda/4$ with respect to each other at right angles to the direction of web travel, wherein $\lambda$ is the wavelength of such electromagnetic radiation, whereby pieces of splicing tape which are small in extent relative to $\lambda$ in the direction of displacement may be readily detected.

* * * * *